United States Patent [19]

Baykut

[11] Patent Number: 4,787,901

[45] Date of Patent: Nov. 29, 1988

[54] TWO-WAY ACTING VALVE AND CARDIAC VALVE PROSTHESIS

[76] Inventor: Doguhan Baykut, Senator-Balcke-Str. 56, D-2800 Bremen 61, Fed. Rep. of Germany

[21] Appl. No.: 946,385

[22] Filed: Dec. 23, 1986

Related U.S. Application Data

[63] Continuation-in-part of Ser. No. 754,241, Jul. 11, 1985, abandoned.

[30] Foreign Application Priority Data

Jul. 17, 1984 [DE] Fed. Rep. of Germany ....... 3426300

[51] Int. Cl.$^4$ ............................................. A61F 2/24
[52] U.S. Cl. ...................................................... 623/2
[58] Field of Search ........................................ 623/1, 2

[56] References Cited

U.S. PATENT DOCUMENTS 3,491,376  1/1970  Shiley .
4,306,319  12/1981  Kaster ..................................... 623/2

FOREIGN PATENT DOCUMENTS 1538204  1/1979  United Kingdom .
2007333  5/1979  United Kingdom .

OTHER PUBLICATIONS

Lenne et al., "Total Opening Valves for a Ventricular Prosthesis," *Medical and Biological Engineering*, pp. 409–517, (Jul. 1975).

*Primary Examiner*—Richard J. Apley
*Assistant Examiner*—James Prizant
*Attorney, Agent, or Firm*—Christie, Parker & Hale

[57] ABSTRACT

A two-way acting valve is provided which comprises a pair of generally cylindrical ducts in longitudinally overlapping relation one of whose uses is as a cardiac valve prosthesis. The ducts are formed in part by a common wall which is deformed by the pressure of fluid flowing through the ducts and in accordance with the direction of flow to open a respective one of the ducts and to at least partially close the respective other of the ducts to control the flow of fluid through the valve. Modifications of the inventions are also shown which simplify attachment of the valve when it is used as a cardiac valve prosthesis.

21 Claims, 4 Drawing Sheets

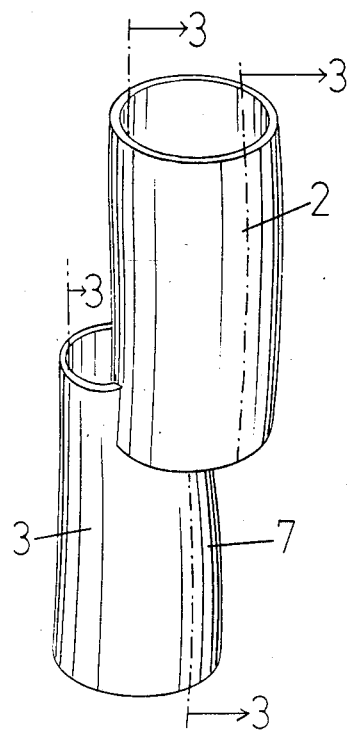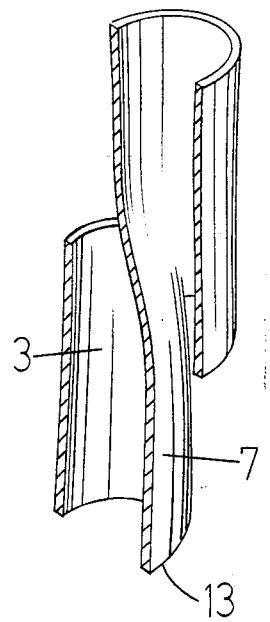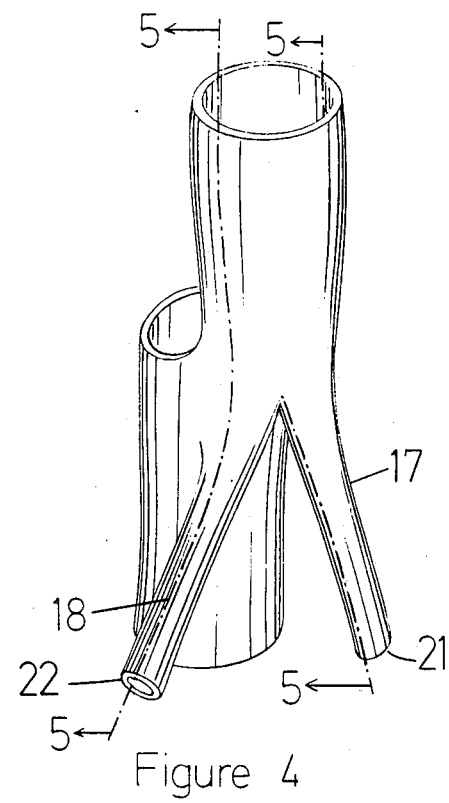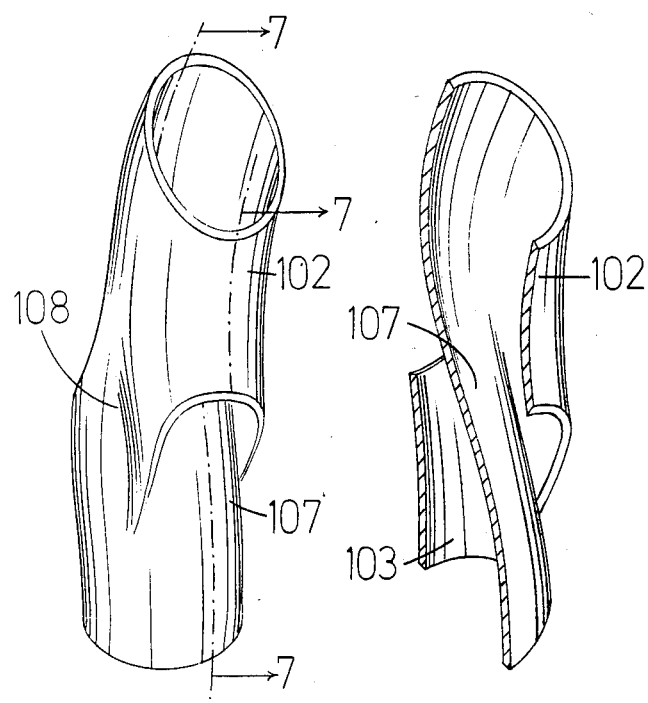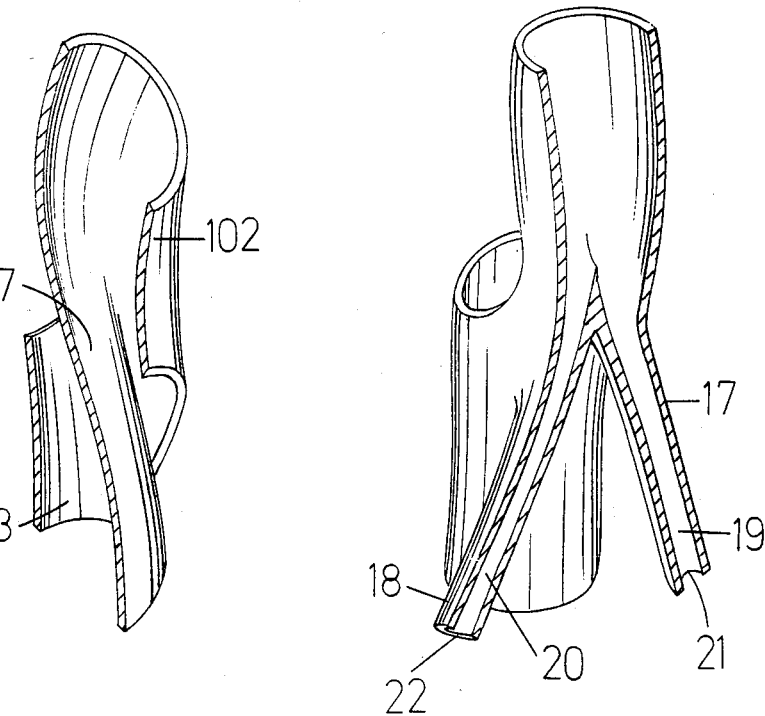
Figure 2
Figure 3
Figure 4
Figure 6
Figure 7
Figure 5

TWO-WAY ACTING VALVE AND CARDIAC VALVE PROSTHESIS

This is a continuation in part of application Ser. No. 754,241 filed July 11, 1985 (now abandoned).

This invention relates to a valve having two flow channels for the flow of a fluid, in which fluid is allowed to flow in one or the other of the channels according to the direction of flow of the fluid.

While the valve shown may be used for many non-medical applications, it is particularly advantageous when used as prosthesis for a cardiac valve. The valve is shown and described herein in the form particularly adapted for such application, but it should be understood that this is not to be taken as a limitation on the general application of the valve.

Many prior art cardiac valve prostheses generally consist of a substantially circular member which is attached, as by suturing. The valve bodies may be noncircular to conform more closely to the shape of the body passage to which they are applied. All of these paior art devices include an occluder, usually in the form of a disc, ball or similar device which cooperates with a complimentary seat in the valve body to mechanically open and close the passageway. This type of prosthesis carries the risk of intravascular blood coagulation, at least partial destruction of blood cells and of hemodynamic disturbances due to the high strain placed on the structural elements. In order to counteract the possibility of undesirable clotting, the patient is required to take anticoagulants on a continuous basis. In addition to the general inconvenience and dependency that this causes, the patient is also subject to disability due to the lack of desirable clotting which is, of course, also deterred. These valves are also found to have a fairly high regurgitation (leakage of blood through the valve back into the heart) and are relatively short lived which may require re-operation in the cases of patients who live more than a few years with the prosthesis.

SUMMARY OF THE INVENTION

The present invention approaches closely the operation of a natural cardiac valve and eliminates most of the problems which arise from use of mechanical occluders.

The cardiac valve of this invention is intended for insertion in the ascending aorta and comprises a pair of generally cylindrical ducts longitudinally adjacent to each other and having an overlapping portion, the two ducts having a common wall between them which extends through the overlapping portion. The ducts help to define a pair of flow channels for blood to and from the heart. The valve is made of tissue-compatible material to avoid rejection by the body and takes advantage of the change of direction of blood flow in the ascending aorta during systolic and diastolic action of the heart to deflect portions of one or the other of the two ducts to limit the flow of blood to the selected channel. The free end of each of the ducts is made to conform substantially to the adjacent cross section of the ascending aorta. As used herein the terms "distal" and "proximal" are used in reference to location with respect to the heart in accordance with medical convention. The proximal or lower end of the systolic duct extends beyond the ostia of the coronary arteries so that blood flowing therethrough cannot enter the ostia. This helps further to reduce regurgitation. At least a portion of the length of each duct wall which is in contact with the inner wall of the ascending aorta is sutured to the wall of the ascending aorta to hold the prosthesis in place. The channel through which the blood flows is determined by the direction of blood flow and the blood pressure causes the common wall of the ducts to be deflected toward the channel which does not have blood flow effectively closing off such other channel from any regurgiation.

The valve constructed in accordance with the invention can be made in one piece and has no separate moving parts, no critical sealing engagement and no mechanical blocking of blood flow with its attendant disadvantages.

Variations of the invention are made in which the flow ducts are curved in their longitudinal direction to more nearly follow the shape of the ascending aorta in which they are placed and the diameter of each channel may also be varied in the longitudinal direction to provide a smaller entrance into the channel through which the blood is not intended to flow thereby requiring less deflection of the common wall to effect sealing.

It is an object of this invention to provide a valve to limit flow of a fluid through one or the other of two contiguous channels according to the direction in which the fluid is flowing.

It is another object of this invention to provide such a valve which has no separable moving parts.

Still another object of this invention is to provide such a valve which is extremely simple in construction and very durable.

Another object of this invention is to provide such a valve which can advantageously be used as a cardiac valve prosthesis.

It is another object of this invention to provide such a valve which is susceptible to very little regurgitation, i.e., unwanted back flow.

Yet another object of this invention is to provide a two-way valve which can readily be constructed from a variety of materials including tissue compatible synthetic materials which may very advantageously be used when the valve is used as a cardiac valve prosthesis.

These and other objects, features and advantages of this invention will become apparent from the following description in conjunction with the accompanying drawings.

BRIEF DESCRIPTION OF THE DRAWINGS

FIG. 2 is a perspective view of one form of the invention.

FIG. 3 is a cross-sectional view taken on the lines 3—3 in FIG. 2.

FIG. 4 is a view similar to FIG. 2 of a modification of the invention which provides separate flow legs leading to the left and right coronary arteries.

FIG. 5 is a cross-sectional view taken on the lines 5—5 in FIG. 4.

FIG. 6 is a view corresponding to FIG. 2 of a form of the invention modified to conform to the approximate shape of the human aorta.

FIG. 7 is a cross-sectional view taken on the lines 7—7 in FIG. 6.

DETAILED DESCRIPTION OF THE INVENTION

As previously indicated the invention will be described as a cardiac valve prosthesis. However, it should be understood that this use is exemplary only and the valve as disclosed may be used in many other applications.

Figure 1:
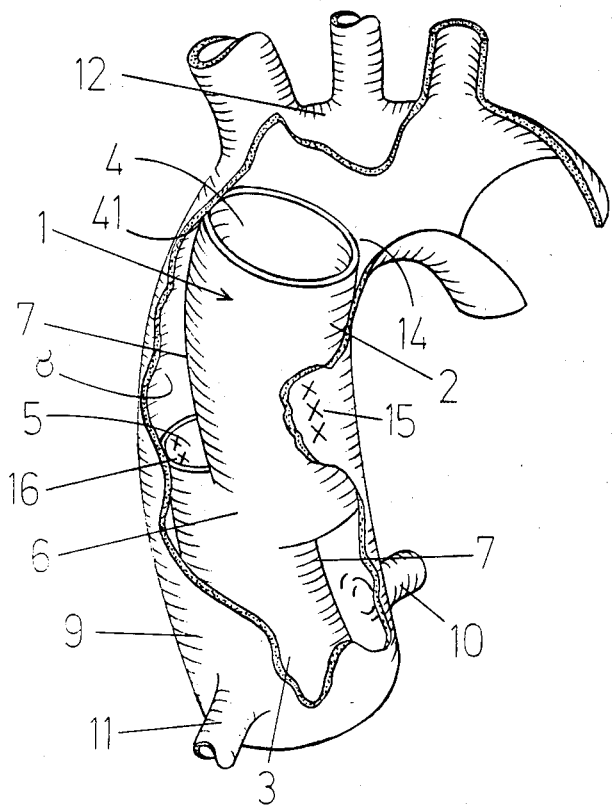
FIG. 1 is a diagrammatic view showing the valve implanted as a prosthesis in a human aorta.

Turning now to FIG. 1, the two way valve of the invention, as indicated generally by the numeral 1 comprises a first cylindrical member or diastolic duct 2 defining a first flow channel 4 and a second cylindrical member or systolic duct 3 defining a second flow channel 5, the two cylindrical members lie adjacent to each other in side-by-side relation and partly overlap each other in the longitudinal direction forming an overlapping section 6 and having a common wall 7 which extends the entire length of the cylindrical members.

As seen in FIG. 1, the valve is placed inside the ascending aorta 9 approximately at the start of the arch of the aorta 12. It is proportioned so that the outer surface of the diastolic duct 2 lies adjacent the inner wall 8 of the ascending aorta throughout the length of the diastolic duct and the portion 41 of the upper or distal end of the diastolic duct 2 lies adjacent the inner wall of the ascending aorta just below the start of the arch of the aorta. The lower or proximal end 13 of the systolic duct extends below the ostia or entrances to the left coronary artery 10 and the right coronary artery 11. The proximal end of the systolic duct is sized to approximate the inner diameter of the ascending aorta which it adjoins taking into account the suturing ring if one is used. The upper or distal end 14 of the diastolic duct is sized to approximate the inner diameter of the ascending aorta which it adjoins. Sutures 15 are made along the middle portion of the diastolic duct to secure it to the ascending aorta. Sutures 16 are made along at least a portion of the length of the systolic duct to secure it to the ascending aorta.

FIGS. 4 and 5 illustrate a modification of the invention in which the lower end of the diastolic duct diverges into a left diastolc extension or leg 17 and a right distolic extension or leg 18 which form a left artery channel 19 and right artery channel 20 respectively. The proximal end 21 of left leg 17 can be sutured to the ostium of left coronary artery 10 and the proximal end 22 of right leg 18 may be sutured to the ostium of right coronary artery 11 to more effectively channel the flow of blood into the arteries.

Figure 8:
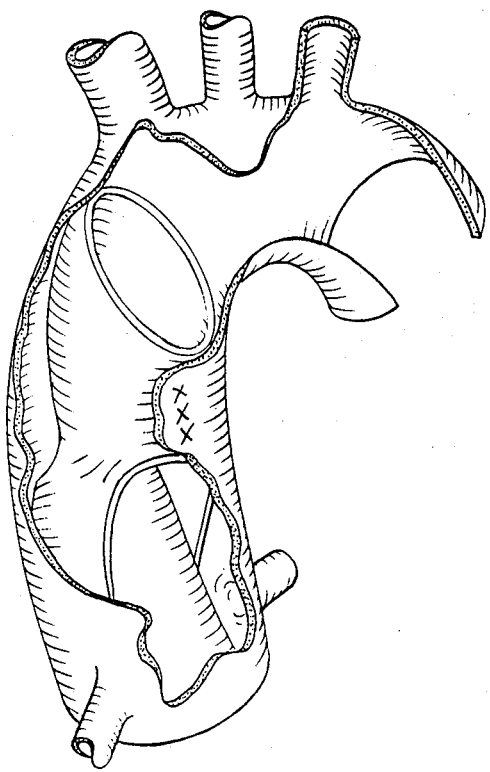
FIG. 8 is a diagrammatic view showing the form of the invention depicted in FIGS. 6 and 7 implanted in the human aorta.

FIGS. 6, 7 and 8 illustrate another modification of the valve shown in FIG. 1. In this modification, the diastolic duct 2 is curved to conform to the beginning of the curve of the arch of the aorta and to provide a smoother laminar flow in the two ducts. The overlapping portion 108 between the two ducts is made larger and constructed with a smoother transition to further avoid mechanical damage to blood cells.

Figures 11, 12:
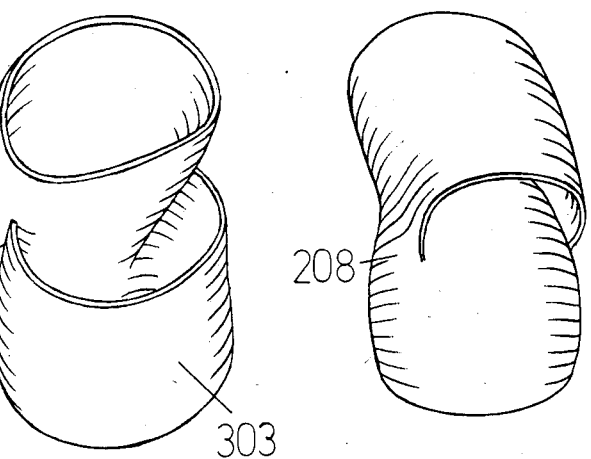
FIG. 11 is a view similar to FIG. 2 showing another modified form of the invention.
FIG. 12 shows a modified form of the valve in FIG. 11.

FIG. 11 illustrates another modification of the invention in which the diastolic duct 302 and the systolic duct 303 are made much shorter. As shown in FIG. 11, the transition section 308 is indicated as a typical intersection between two cylindrical members and is similar to the transaction section shown in FIGS. 1 through 3.

Figure 13:
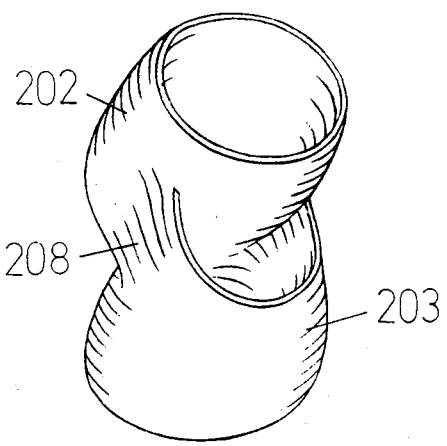
FIG. 13 is another view of the form of the invention shown in FIG. 12.

FIGS. 12 and 13 show a modification in which the transition section 208 is shown as smoothly blending from duct 202 to duct 203.

Figure 14:
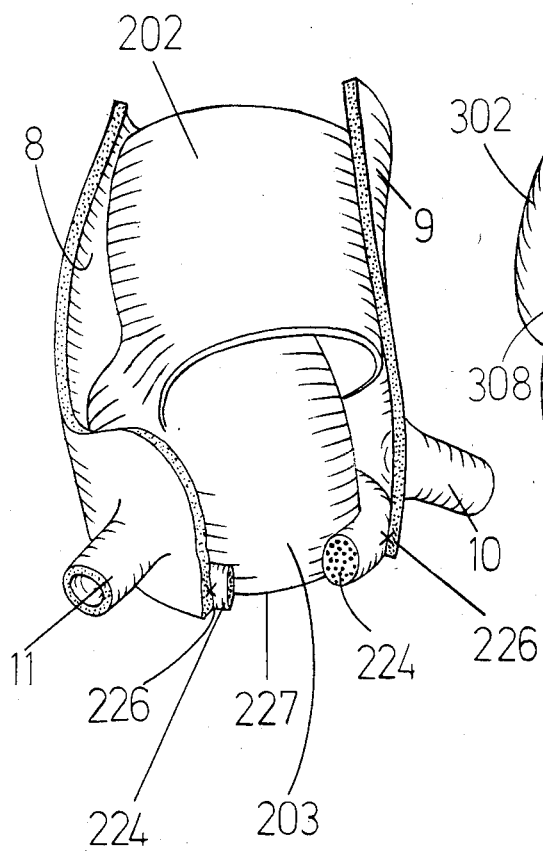
FIG. 14 shows the invention of FIG. 11 implanted in the human aorta.

In the modification shown in FIGS. 11 through 14 the diastolic and systolic ducts are shown as overlapping a much greater portion of their lengths so that the ducts will be more rigidly self supporting and can be attached to the ascending aorta by a suturing ring such as the ring 224 in FIG. 14. The shortened version of the valve illustrated in FIGS. 11 through 14 is capable of much simpler and less time consuming attachment to the human aorta when used as a heart valve prosthesis permitting a much shorter total operating time. The suturing ring 224 is secured to the proximal or lower end 227 of systolic duct 203 by any known suitable means such as, but not limited to, welding or adhesive. The entire assembly is attached to the aorta by sutures 226 extending around the circumference of the aortic root.

Figure 20:
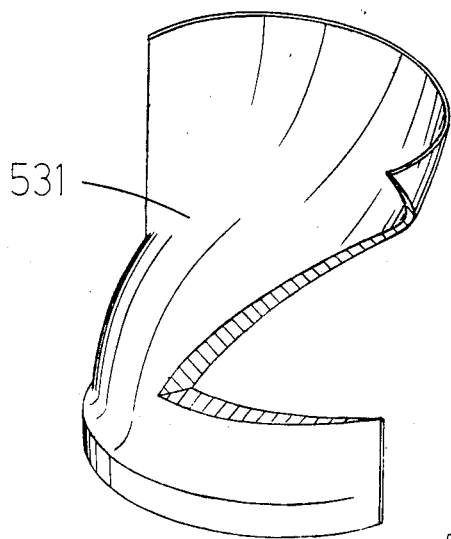
FIG. 20 is a cross-sectional view taken on the lines 20—20 in FIG. 19.
Figure 19:
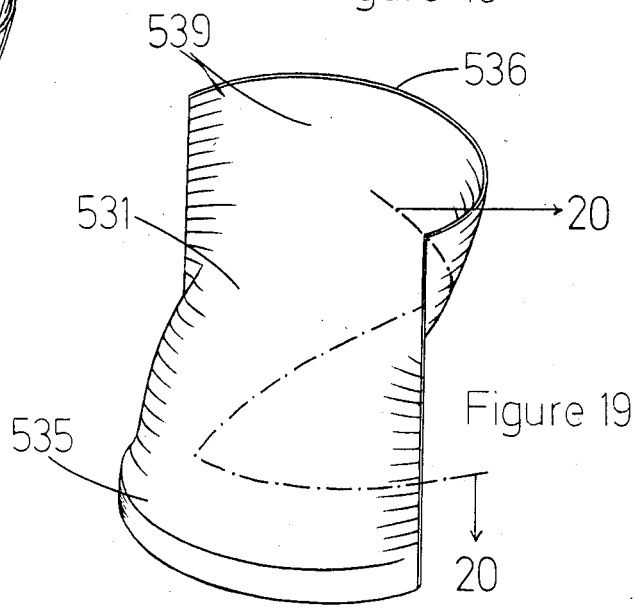
FIG. 19 is a perspective view of the leaflet which forms the transitional wall which creates the two channels in the form of the invention shown in FIGS. 16 through 18.
Figure 15:
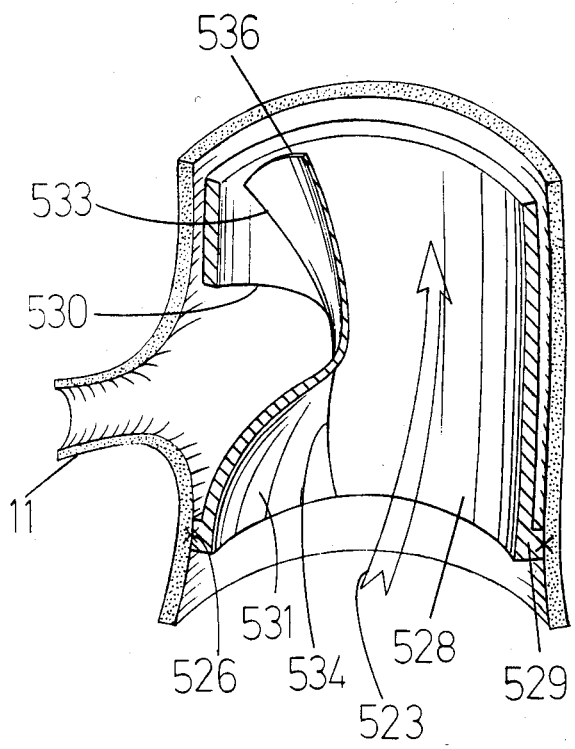
FIG. 15 is a diagrammatic cross-sectional view of another modified form of the invention implanted in the human aorta and showing the valve in conditions which prevail under systolic blood flow.
Figure 16:
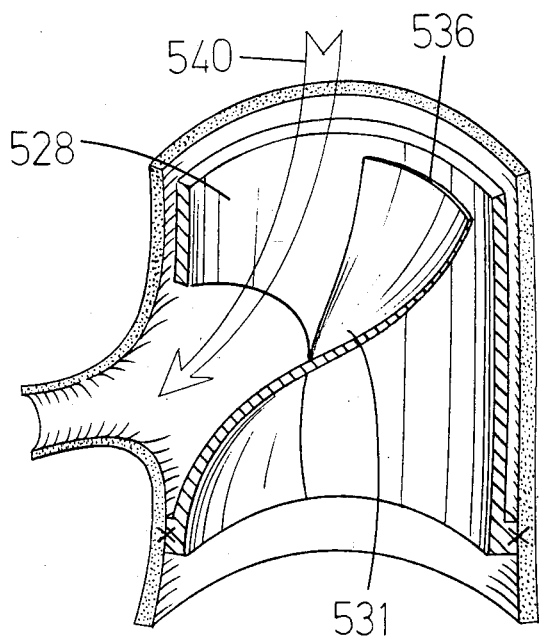
FIG. 16 is a drawing similar to FIG. 15 but showing the valve in conditions which prevail under diastolic blood flow.
Figure 17:
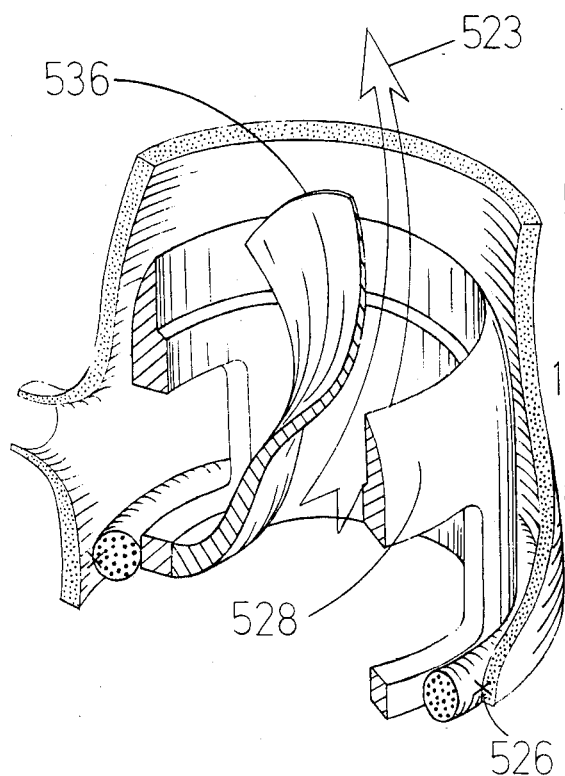
FIG. 17 shows a modified form of the invention shown in FIGS. 15 and 16 implanted in the human aorta with portions of the ascending aorta broken away for clarity and showing the valve in conditions which prevail under systolic blood flow.
Figure 18:
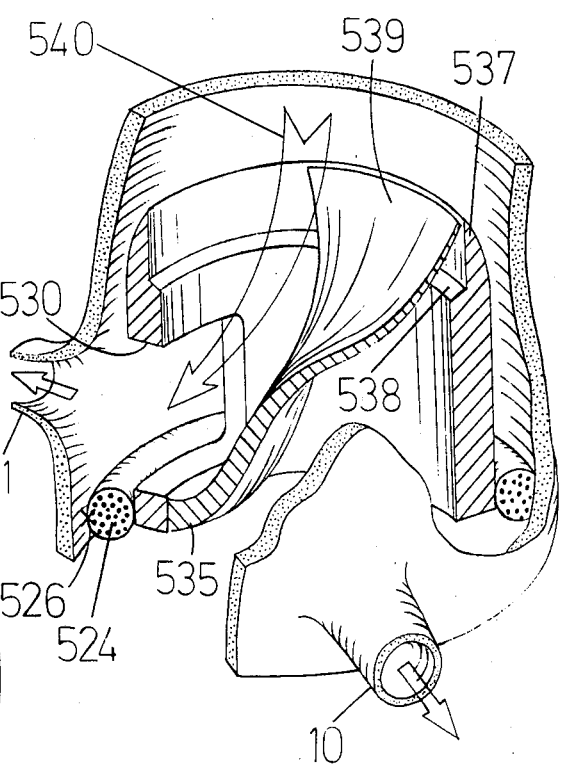
FIG. 18 shows the valve of FIG. 17 under diastolic blood flow.

Still another modification of the invention is shown in FIGS. 15 through 20. In this version the valve body 528 is made to conform closely to the inner wall of the ascending aorta adjacent the entrance to the coronary arteries. The valve body has an integral reinforcing ring 529 by which the valve body can be sutured or otherwise secured to the inner wall of the ascending aorta at a point below the ostia of the coronary arteries. The proximal edges of the valve body may be rounded or faired to present a smooth contour (not shown) to systolic blood flow to help avoid flow disturbances which may cause damage to blood cells. The valve body is provided with a window or opening 530 which extends around a portion of the circumference of the valve body to at least include the arc encompassed between the left and right coronary arteries. The valve leaf 531 is integrally formed with the reinforcing ring 529 or is welded or otherwise permanently secured to the reinforcing ring. The valve leaf 531 has a width substantially equal to the width of the window 530 and a portion of the edge 533 of the leaf which is adjacent to the edge 534 of window 530 may be permanently secured thereto by welding or other suitable means. The thickness of the valve leaf may be tapered from its base 535 to a smaller thickness at its tip 536. The leaf may also be constructed with a compound taper reducing to a smaller thickness from the base to the tip and from its center to each of its sides as best seen in FIG. 20. Optionally, the valve body may be constructed without the reinforcing ring 529 and may be attached to the ascending aorta by an annular sewing or suturing ring 524 which is secured to the valve body by welding, cementing or other suitable means and to the ascending aorta by sutures 526 all as shown in FIG. 18. As another option the upper end of the valve body 528 may be provided with a tapered portion 537 and a circumferential valve seat 538 around its periphery also seen in FIG. 18.

It should be understood that in all of the disclosed forms of the valve, any of the edges of the valve which are presented to flowing blood, especially those facing systolic flow, may be rounded or faired to help avoid turbulence or mechanical damage to blood cells. It is also optional to use a suturing ring where none is shown or to dispense with a suturing ring which is shown and to suture the prosthesis directly to body tissue or to use other available means of attaching the prosthesis.

When the invention is intended for use as a prosthesis for a cardiac valve, the valve of the invention is preferably made of a synthetic material which is tissue-compatible, which may be welded and/or cemented and/or sutured and which has good elastic deformation characteristics so that it will return to its original shape after being deformed as hereinafter described in response to the flow of blood. Examples of such materials are polyurethane, polypropylene, or polytetrafluoroethylene. Biological materials may also be used, such as bovine pericardium.

OPERATION OF THE INVENTION

Figure 9:
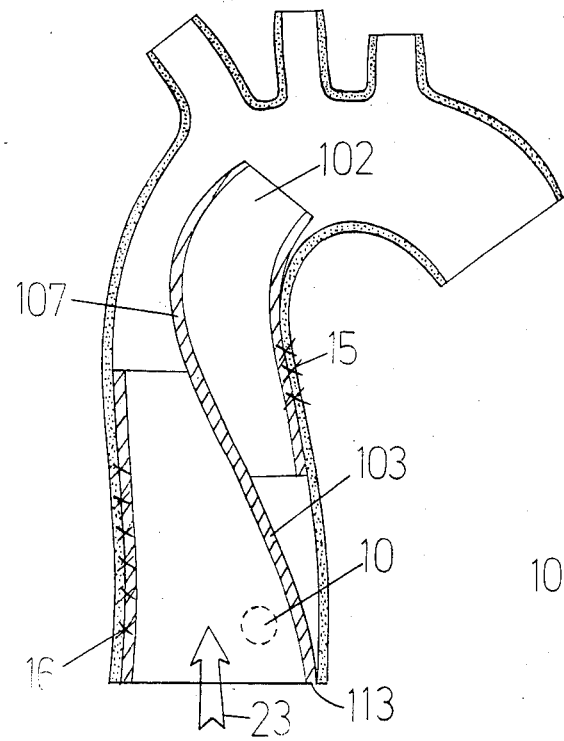
FIG. 9 is a diagrammatic view in cross-section of the valve shown in FIG. 2 indicating its condition when blood is flowing out of the heart into the ascending aorta (systole).
Figure 10:
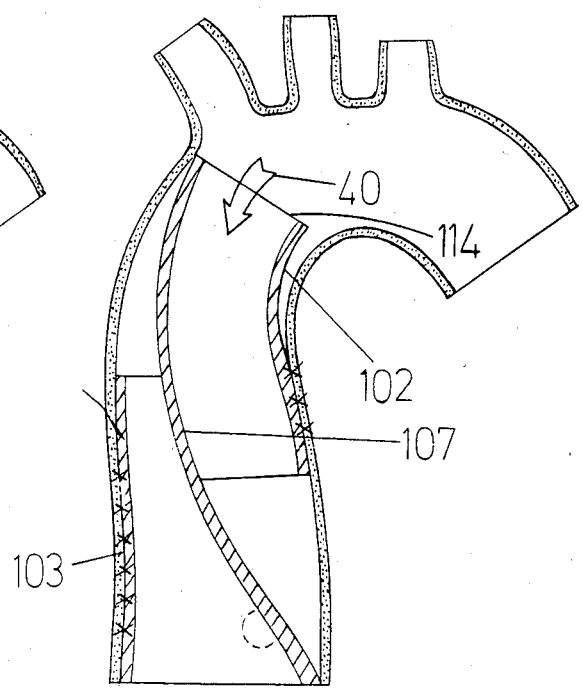
FIG. 10 is a view similar to FIG. 9 but showing the prosthesis in the condition when blood is flowing from the ascending aorta toward the heart into the coronary arteries (diastole).

FIG. 9 shows the invention in the form shown in FIGS. 2 and 3 in the systolic mode when blood is flowing in the direction indicated by the arrow 23. As previously indicated the lower or proximal end 113 of the systolic duct 103 closely approximates the inner diameter of the ascending aorta which it adjoins so that blood flow is confined to the systolic duct 103 and bypasses the coronary arteries. When the blood passes the upper end of the systolic duct it flows between the inner wall of the ascending aorta and the common wall 107 of the diastolic duct 102 causing the duct 102 to deform and allowing the passage of blood into the arch of the aorta. When systolic blood flow ceases the resiliency or elasticity of the material from which the ducts are made causes duct 102 to return to its original or normal configuration indicated in FIG. 10. The portion of the common wall 107 which is common to both ducts also returns to its original condition reducing the size of the passage through duct 103 and expanding the overlapping portion of duct 102. The distal end 114 of the diastolic duct 102, encompasses substantially all of the cross-sectional area of the ascending aorta which it adjoins. As best seen in FIG. 10, when the heart expands, diastolic flow of blood begins in the direction of the arrow 40 and blood flows through the diastolic duct 102 and into the coronary arteries 10 and 11. Deformation of common wall 107 also occurs further expanding duct 102 and constricting duct 103.

When used as a cardiac valve prosthesis the valve is placed in the ascending aorta with the outer wall of the systolic duct in contact with the inner wall of the ascending aorta at a point approximately midway between the ostia of the coronary arteries as best seen in FIGS. 9 and 10, with its proximal end 113 at a point below the coronary arteries and in proximity to the inner wall of the ascending aorta around substantially its entire circumference. The diastolic duct is in contact with the inner wall of the ascending aorta and has its proximal end above the ostia of the coronary arteries. This assures that diastolic blood flow into the coronary arteries will be unrestricted.

In the forms of the invention shown in FIGS. 15 through 18, valve leaf 531 is so formed and is secured to the valve body 528 in such a manner that in its normal or at rest position the upper or distal end 539 of valve leaf 531 will lie between the longitudinal center of valve body 528 and the perimeter of the valve body. The distal end of the valve leaf is of generally arcuate shape conforming substantially to the circumference of the valve body and will seat against the inner periphery of the valve body when the leaf is deflected by the diastolic flow of blood. In the embodiment shown in FIGS. 17 and 18, the seat 538 and tapered edge 537 of the valve body help to maintain a good seal with the upper end 539 of the valve leaf when the leaf is deflected by diastolic blood flow.

Operation of the embodiment shown in FIGS. 15 through 18 is as follows: When blood flows in the direction of the arrow 523 in FIGS. 15 and 17 (systole), the valve leaf 531 is deflected farther away from the valve body in the direction toward the window 530, helping to avoid unwanted back flow of blood into the coronary arteries. When systolic blood flow ceases, the valve leaf 531 moves resiliently back to its normal or at rest position. When diastolic blood flow in the direction of the arrow 540 begins, valve leaf 531 is deflected farther toward valve body 528 until the valve leaf seats against the inner periphery of the valve body. The distal end 539 of the valve leaf will seat against the valve seat 538 in the case of the embodiment shown in FIGS. 17 and 18. When diastolic blood flow ceases, the valve leaf returns to its normal or at rest position to await the next systolic flow. The above cycle of operation continues to be repeated in response to the normal contraction and expansion of the heart muscle.

It can be seen that this invention has provided an effective and efficient two-way valve with no separable moving parts and which can be used as a cardiac valve prosthesis and for many other purposes. It is be understood that the invention disclosed herein is not limited to the details of construction and arrangement of parts illustrated in the accompanying drawings, but is capable of being practiced or carried out in various ways. Furthermore, the terminology employed herein is for the purpose of description only and is not to be considered as limitation.

It is obvious to those skilled in the art that although the invention has been shown and described in a limited number of preferred embodiments many variations may be made in the form and structure here presented without departing from the scope of the present invention as set forth in the appended claims.

What is claimed is:

1. A heart valve prosthesis adapted to be implanted into the ascending aorta, the valve prosthesis comprising a pair of ducts which define an orifice through the aorta and which are separated from each other at least along a portion of their length by a common wall, the common wall being deformable under the pressure of blood in the ascending aorta to selectively open a first one of the ducts and at least partially close the second one of the ducts.

2. The heart valve prosthesis according to claim 1 wherein the first one of the ducts is caused to open under systolic pressure.

3. The heart valve prosthesis according to claim 1 wherein the proximal end of the duct that opens under systolic pressure is configured to be attached around the entire inner circumference of the ascending aorta proximal the coronary arteries.

4. The heart valve prosthesis according to claim 1 wherein the second one of the ducts opens at diastolic pressure.

5. A heart valve prosthesis comprising an elongated valve body adapted to be implanted into the ascending aorta, the valve body comprising a diastolic duct on the distal end and a systolic duct on the proximal end, wherein the ducts define an orifice through the aorta, the ducts being offset horizontally from each other and connected together by a flexible common wall, the proximal end of the systolic duct configured to a attached around the entire inner circumference of the aorta, proximal the coronary arteries.

6. The heart valve prosthesis according to claim 5 wherein the valve body is deformable under pressure of blood in the ascending aorta so that, during ventricular systole, blood flows from the heart through the systolic duct, and the diastolic duct is caused to at least partially close.

7. The heart valve prosthesis according to claim 5 wherein the valve body is deformable under the pressure of blood in the ascending aorta so that under diastolic pressure the diastolic duct is opened to accommodate blood flow through the diastolic duct and into the coronary arteries and the systolic duct is at least partially closed.

8. The heart valve prosthesis according to claim 5 wherein the proximal end of the diastolic duct diverges into two legs, one leg configured to be connected to the left coronary artery and the other leg configured to be connected to the right coronary artery.

9. A heart valve prosthesis adapted to be implanted into the ascending aorta, the prosthesis comprising a hollow cylindrical valve body having an opening through a portion of its circumference and a flexible valve leaf which divides the valve body into two ducts, a diastolic duct and a systolic duct, and which is connected on one end to the proximal end of the valve body, the distal end of the valve leaf being configured to be deflected under systolic pressure to open the systolic duct and to partially close the diastolic duct.

10. The heart valve prosthesis according to claim 9 wherein the proximal end of the valve leaf is connected to the proximal end of the valve body along at least the entire circumference of the valve body opening.

11. The heart valve prosthesis according to claim 9 wherein the proximal end of the valve body is configured to be attached around the entire inner circumference of the aorta, proximal the coronary arteries.

12. The heart valve prosthesis according to claim 9 wherein the cross-sectional thickness of the valve leaf increases from each of its side edges toward its central portion over at least part of its end-to-end length.

13. The heart valve prosthesis according to claim 9 wherein the distal end of the valve leaf is of generally arcuate shape conforming substantially to the circumference of the valve body and configured to seat against the inner periphery of the valve body to thereby at least partially close the systolic duct when the leaf is deflected during diastolic blood flow.

14. The heart valve prosthesis according to claim 9 wherein the valve leaf has a width substantially equal to the width of the opening.

15. The heart valve prosthesis according to claim 9 wherein the valve leaf is tapered from a relatively larger thickness at its proximal end to a smaller thickness at its distal end.

16. The heart valve prosthesis according to claim 9 wherein the valve leaf has a compound taper reducing to a smaller thickness from the base to the tip and from the center to each of its sides.

17. The heart valve prosthesis according to claim 9 wherein the opening extends around at least a sufficient portion of the circumference of the valve body so that when the valve prosthesis is implanted, the opening is large enough to encompass both the left and right coronary arteries.

18. A heart valve prosthesis comprising a generally cylindrical valve body adapted to be inserted in conforming relation to the ascending aorta to define an orifice therethrough, the valve body being divided into two ducts by a wall common to each of the two ducts and operatively integral with the valve body, at least a portion of the length of the common wall being capable of movement toward and away from the opposite wall of each of the two ducts which it defines, the common wall having a fixed end operatively integral with the valve body and a free end, wherein the cross-sectional thickness of the common wall increases from its free end toward its fixed end.

19. A heart valve prosthesis adapted to be implanted into the ascending aorta, the valve prosthesis comprising a pair of ducts, a systolic duct and a diastolic duct, which define an orifice through the aorta and which are separated from each other at least along a portion of their length by a common wall, the common wall being deformable under the pressure of blood in the ascending aorta to thereby increase the cross-section to blood flow under systolic pressure in the systolic duct by opening the systolic duct and, at the same time, to thereby decrease the cross-section to blood flow in the diastolic duct by at least partially closing the diastolic duct.

20. The heart valve prosthesis according to claim 19 wherein the proximal end of the systolic duct is configured to be attached around the entire inner circumference of the ascending aorta proximal the coronary arteries.

21. The heart valve prosthesis according to claim 19 wherein the diastolic duct opens from its at least partially closed position under diastolic pressure.

* * * * *